US00PP23499P2

(12) United States Plant Patent
Dirr

(10) Patent No.: US PP23,499 P2
(45) Date of Patent: Mar. 26, 2013

(54) CRAPEMYRTLE PLANT NAMED 'GAMAD VIII'

(50) Latin Name: ***Lagerstroemia* hybrid**
Varietal Denomination: GAMAD VIII

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 33 days.

(21) Appl. No.: 12/931,792

(22) Filed: Feb. 9, 2011

(51) Int. Cl.
*A01H 5/00* (2006.01)

(52) U.S. Cl. ..... Plt./252

(58) Field of Classification Search ..... Plt./252
See application file for complete search history.

*Primary Examiner* — June Hwu
(74) *Attorney, Agent, or Firm* — Klarquist Sparkman, LLP

(57) ABSTRACT

A new and distinct cultivar of crapemyrtle, 'GAMAD VIII', is provided. 'GAMAD VIII' is a *Lagerstroemia indica*×*Lagerstroemia fauriei* hybrid. The new variety is characterized by intermediate-size, upright growth habit, good mildew resistance, and earlier flowering with abundant pale pink flowers.

2 Drawing Sheets

Latin name of the genus and species of the plant claimed: 'GAMAD VIII' is a crapemyrtle plant that is a *Lagerstroemia* hybrid.

Variety denomination: The new crapemyrtle plant claimed is of the variety denominated 'GAMAD VIII'.

BACKGROUND OF THE INVENTION

The present invention relates to the discovery of a new and distinct cultivar of the ornamental flowering shrub *Lagerstroemia indica*×*Lagerstroemia fauriei*, commonly known as crapemyrtle, and hereafter referred to by the varietal denomination 'GAMAD VIII', as herein described and illustrated.

The new crapemyrtle originated from open-pollinated seed of 'Pocomoke', an unpatented seedling. 'GAMAD VIII' was selected from plants being grown in a cultivated area at Dearing, Ga. from these seeds. The seedlings were planted in containers and selections were made for plants based on the following criteria: 1) intermediate, upright growth habit; 2) good mildew resistance; 3) early flowering; and 4) flower color and quality. 'GAMAD VIII' was selected in 2002.

Asexual reproduction by traditional vegetative cuttings since 2003 at Dearing, Ga. and in Athens, Ga. has shown that the distinguishing characteristics of this new crapemyrtle variety 'GAMAD VIII' are stable and reproduced true-to-type in successive generations.

SUMMARY OF THE INVENTION

The new crapemyrtle plant variety 'GAMAD VIII' has not been observed under all possible environmental conditions. The phenotype may vary somewhat with variations in environment and cultural practices such as temperature and light intensity without, however, any variance in genotype.

The following combination of traits of my new variety have been repeatedly observed at Dearing, Ga. and Athens, Ga., and are determined to be the unique characteristics of the new crapemyrtle plant variety 'GAMAD VIII':

1. Intermediate size; upright growing habit
2. Good mildew resistance

3. Earlier flowering in mid to late June (USDA Zone 7)
4. Abundant pale pink flowers There were no intermediate-sized, pale pink flowering varieties of crapemyrtle available for comparison. 'GAMAD VIII' is smaller in habit than the variety 'Whit VIII' (U.S. Plant Pat. No. 16,616). In addition, in comparison to the variety 'Whit VIII', my new variety has abundant pale pink flowers, is earlier flowering, and is more *Cercospora* resistant. The parent of 'GAMAD VIII' is not currently available. However, this parent differed from 'GAMAD VIII' by being more compact in habit and by having a deep pink to rose flower color.

BRIEF DESCRIPTION OF THE DRAWINGS

The accompanying photographic illustrations show typical specimens in full bloom of the new variety 'GAMAD VIII'. The colors are as nearly true as is reasonably possible in a color representation of this type.

BOTANICAL DESCRIPTION

Figure 1:
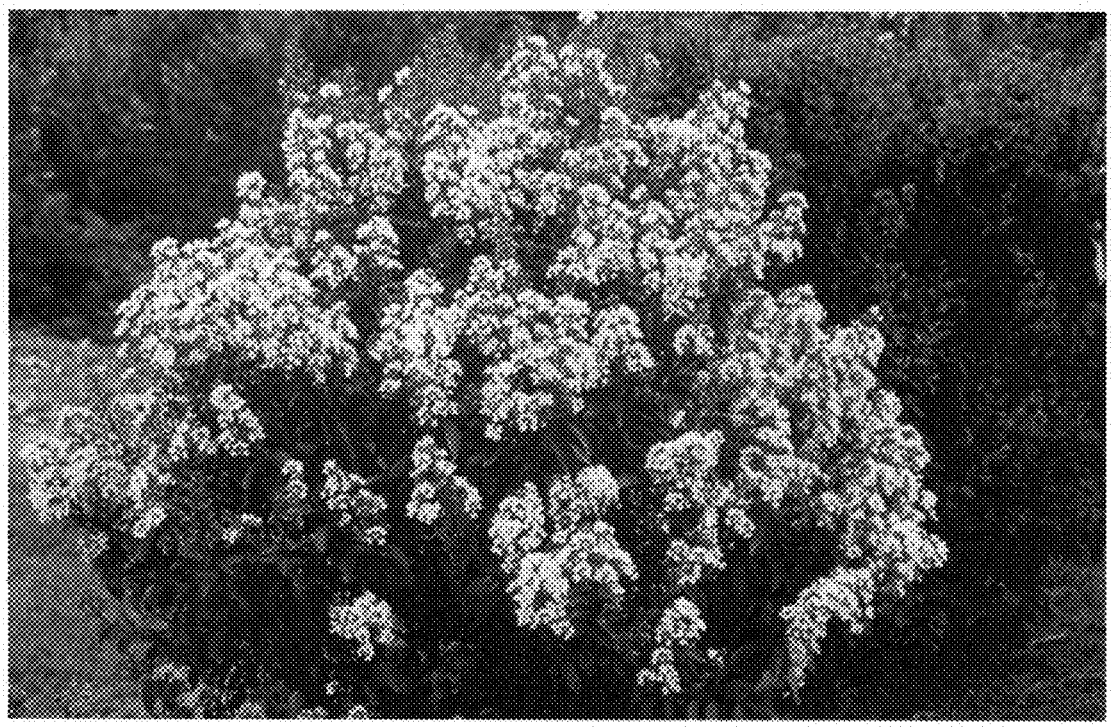
FIG. 1 is a photograph of an eight year old plant of the new variety 'GAMAD VIII'.
Figure 2:
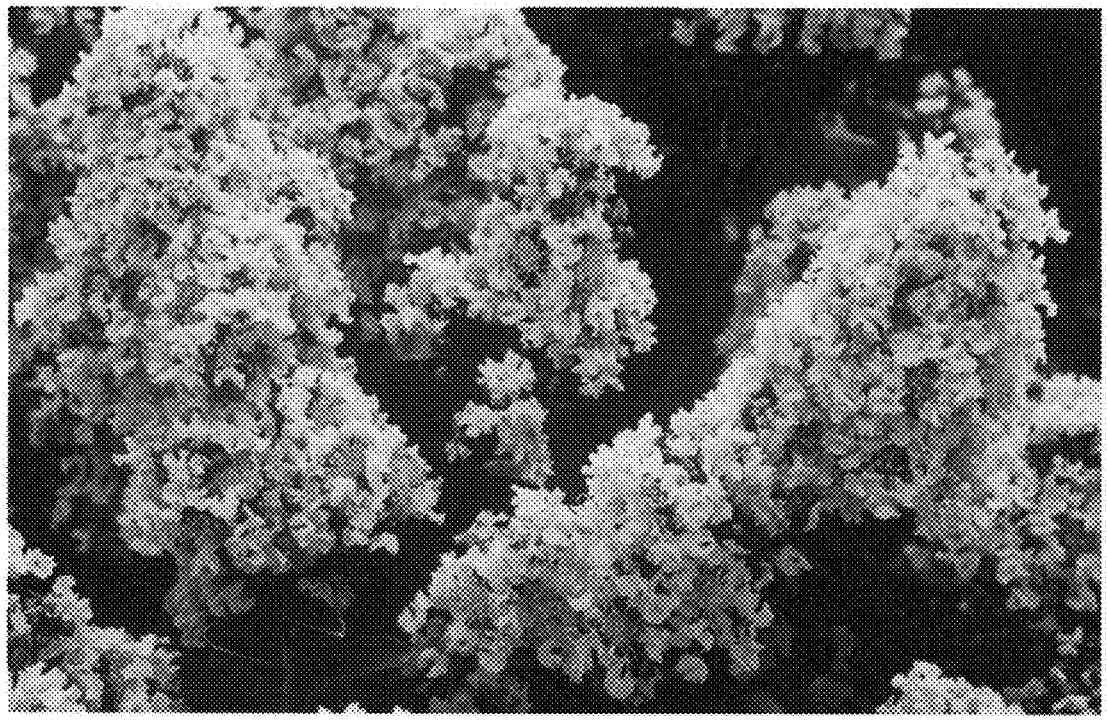
FIG. 2 is a photograph more closely illustrating the flowers of the new variety 'GAMAD VIII' plant of FIG. 1.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and horticultural characteristics of the new variety 'GAMAD VIII'. Where dimensions, sizes, colors, and other characteristics are given, it is to be understood that such characteristics are approximations and averages set forth as accurately as practicable. The descriptions reported herein are from specimen plants grown at Athens, Ga. Data were obtained in summer 2010 on plants that were 6 years old.

PLANT

Habit: Intermediate size, upright growing.
Size:
*Height.*—130 cm.
*Width.*—92 cm.
Branch density: Medium.

STEMS

Color: Brown RHS 200D in first year changing to Greyed-brown RHS 197A in the second year. Mature stem color is greyed-brown RHS 199A.
Diameter: 3 mm.
Pubescence: Observed along edges.
Exfoliation: Strips.
Shape: Squared.
Pith:
*Type.*—Solid.
*Diameter.*—1 mm.
*Color.*—Green RHS 137D.
Odor (of bruised stem): None.
Lenticels: None.
Internode length: 28 mm to 34 mm.

VEGETATIVE BUDS

Arrangement: Sub-opposite to alternate.
Type: Imbricate, ovoid.
Size:
*Length.*—3 mm.
*Width.*—1 mm.
Scale number: 3.
Scale color: Greyed-brown RHS 199D.
Position/disposition: 30 degrees to stem.
Number at node: 1.
Pubescence: None.
Shape: Ovoid to rounded.

LEAF SCAR

Shape: Raised half ellipse.
Vascular bundle traces: None observed.
Pubescence: None.
Position of bud: Directly on top.
Color: Green RHS 137A.
Size:
*Height.*—1 mm.
*Width.*—2 mm.

TRUNK OR LARGE STEMS

Color: Grey-brown RHS 199C.
Size of stem on which exfoliation begins: 16 mm, with some peeling occurring.
Diameter: 16 mm.
Texture: Slightly exfoliating without any noted color difference.

LEAF

Color at emergence:
*Upper leaf surface.*—Yellow-green RHS 148A.
*Lower leaf surface.*—Yellow-green RHS 148B.
Color during summer season (no appreciable fall color difference noted):
*Upper leaf surface.*—Green RHS 137A.
*Lower leaf surface.*—Green RHS 138B.
Mature size:
*Length.*—54 mm (on average).
*Width.*—26 mm (on average).
Apex: Acuminate.
Base: Acute.
Margin: Entire.
Shape: Obovate.
Vein color: Green-purple RHS 183B.
Pubescence: Finely hairy on entire upper leaf surface, only observed along veins and midrib on lower surface.
Arrangement on stem: Sub-opposite to alternate.
Venation: Pinnate.
Texture: Leathery.
*Thickness.*—0.5 mm thick.
*Degree of waxiness of surfaces.*—Moderately waxy.

PETIOLE

Length: 2.5 mm.
Cross-sectional shape: Mostly rounded to semi-oval.
Color: Greyed-purple RHS 183B on top and Red-purple RHS 59B underneath.
Pubescence: Finely hairy.
Diameter: 1 mm.

FLOWER BUDS

Size:
*Length.*—6.5 mm.
*Width.*—5 mm.
Color: Red-purple RHS 60A.
Shape: Rounded.
Pubescence: None.
Time of full maturity: Mid to late June (USDA Zone 7).
Time range for showiness: Approximately 9 to 11 weeks for buds and flowers.

FLOWER

Inflorescences:
*Type.*—Paniculate.
*Size.*—Length: 9.5 cm. Width: 7.5 cm.
*Color at emergence.*—Red-purple RHS 62C.
*Color at full bloom.*—Red-purple RHS 65A.
*Color at fading.*—Red-purple RHS 69A.
*Peduncle.*—Length: Typical length 12.7 cm to 15.2 cm. Color: Purple-red RHS 183D. Pubescence: Finely hairy along edges. Individual flowers: Single, solitary, six petaled, width typically about 19 mm to 38 mm, length typically about 19 mm to 38 mm, held in a paniculate inflorescence.
Petals:
*Number.*—6.
*Size.*—Length: 21 mm. Width: 14 mm.
*Shape.*—Fan-shaped.
*Apex.*—Ruffled, rounded.
*Base.*—Sagittate.
*Margin.*—Ruffled.
*Pubescence.*—None.
*Texture.*—Smooth.
*Color at peak of bloom.*—Upper surface: Red-purple RHS 65A. Lower surface: Red-purple RHS 69B.

*Pedicels*.—Color: Greyed-purple RHS 185A. Pubescence: None. Length: 6.5 mm. Flowers per Inflorescence: Typically 150-200.

MALE REPRODUCTIVE STRUCTURES

Number: 6 (fertile); 20 to 30 (sterile).
Pollen color: Yellow-orange RHS 14A.
Pubescence: None.
Anther:
*Size*.—(Both fertile and sterile). Length: 1.5 mm. Width: 1 mm.
*Color*.—Yellow RHS 13A (fertile); Yellow RHS 13A (sterile).
Filament:
*Size*.—7 mm to 9 mm (fertile); 7 mm to 11 mm (sterile).
*Color*.—Yellow RHS 4B (fertile); Yellow RHS 4B (sterile).

FEMALE REPRODUCTIVE STRUCTURES

Pistil:
*Size*.—Length: 16 mm. Width: 0.5 mm.
*Position*.—Superior.
*Pubescence*.—None.
Stigma:
*Shape*.—Rounded.
*Color*.—Yellow-green RHS 148A.
*Pubescence*.—None.
Style:
*Length*.—16 mm.
*Shape*.—Linear.
*Color*.—Greyed-yellow RHS 160B.
*Pubescence*.—None.
Ovary:
*Shape*.—Oval to round.
*Number*.—One per flower.
*Pubescence*.—None.
*Size* (*diameter*).—2 mm.
*Color*.—Yellow RHS 3C.

FRUIT

Type: Dehiscent, six-valved capsule.
Size:
*Length*.—8 mm.
*Width*.—6.5 mm.
Color during ripening:
*Early*.—Greyed-orange RHS 165B at tip; about Yellow-green RHS 146C at base.
*Mid*.—Yellow-green RHS 146B.
*Late*.—Brown RHS 200B (before splitting); Greyed-orange RHS 165A (after seed dispersal).
Shape: Broad-ellipsoidal.
Number per infructescence: 80 to 90.
Pubescence: None.
Number of carpels: 6.
Persistence (effective period): 3 months holding into winter in Athens, Ga.

SEED

Shape: Oval-rounded.
Size:
*Length*.—5 mm.
*Width*.—2.5 mm.
Color: Brown RHS 200B (seed); about Greyed-orange RHS 164C (wing).
Number per fruit: 15 to 30.
Pubescence: None.

DISEASE RESISTANCE

Good resistance to powdery mildew and more resistant to *Cercospora* than 'Whit VIII' (U.S. Plant Pat. No. 16,616 P2). The new variety is not completely resistant to mildew, but exhibits a higher resistance to mildew than some other cultivars.

What is claimed is:

1. A new and distinct variety of crapemyrtle plant named 'GAMAD VIII', substantially as illustrated and described herein.

* * * * *